000000000000000
United States Patent [19]

Wada et al.

[11] 4,306,019

[45] Dec. 15, 1981

[54] METHOD OF DIFFERENTIAL ESTIMATION OF GLUTAMIC ACID-OXALACETIC ACID TRANSAMINASE ISOZYME

[75] Inventors: Hiroko Wada, Ikoma; Hiroyasu Teranishi, Musashino, both of Japan

[73] Assignee: Eiken Chemical Co., Ltd., Tokyo, Japan

[21] Appl. No.: 767,025

[22] Filed: Feb. 9, 1977

[30] Foreign Application Priority Data

Feb. 16, 1976 [JP] Japan ................................. 51/16342

[51] Int. Cl.$^3$ ..................... G01N 33/54; G01N 33/68; G01N 33/52
[52] U.S. Cl. ..................................... 435/7; 23/230 B; 424/8; 424/12; 435/15; 435/16
[58] Field of Search ............... 424/2, 8, 12; 23/230 B; 195/63, 103.5 A

[56] References Cited

U.S. PATENT DOCUMENTS 3,932,221  1/1976  Pfleiderer ........................... 424/2 X
4,012,285  3/1977  Pfleiderer ........................... 424/2 X

FOREIGN PATENT DOCUMENTS 50-19918  3/1975  Japan .

*Primary Examiner*—Anna P. Fagelson
*Attorney, Agent, or Firm*—Armstrong, Nikaido, Marmelstein & Kubovcik

[57] ABSTRACT

A method is disclosed for differential estimation of glutamic acid-oxalacetic acid transaminase isozyme which comprises estimating m-GOT by: preparing an immuno conjugate by adding an anti-s-GOT obtained by immunizing a mammal with purified s-GOT as antigen extracted from the blood or the tissue of the mammal into the human serum; adding sensitized particles which are allowed to couple said anti-s-GOT antibody to insoluble particles; and completely absorbing said s-GOT in said human serum.

4 Claims, No Drawings

METHOD OF DIFFERENTIAL ESTIMATION OF GLUTAMIC ACID-OXALACETIC ACID TRANSAMINASE ISOZYME

This invention relates to a method of differential estimation of glutamic acid-oxalacetic acid transaminase isoyzme.

BACKGROUND OF THE INVENTION

The level of glutamic acid-oxalacetic acid transaminase (hereafter designated as GOT), in diseases of the liver and heart varies in accordance with the degree of disorder of these organs. Therefore, the measurement of GOT level has a very high clinical and diagnostic significance.

It is known that GOT is composed of two kinds of isozymes which are located in different parts of the cells. One is in the supernatant fraction of cells (hereafter designated as s-GOT) and the other is in the mitochondria (hereafter designated as m-GOT).

The differential estimation of GOT isozyme therefore also has a very high clinical significance just as does the measurement of total GOT.

Conventionally, several methods including electrophoresis, ion-exchange chromatography, etc. have been reported for the differential estimation of GOT isozyme. These methods, however, necessitate complicated pre-treatment and are limited to use in research laboratories especially equipped to carry out these determinations.

Previously, the present inventors developed a simple and rapid method of differential estimation of GOT isozyme (see Japanese Patent Application No. Sho 48-73157). The object of the present invention is to provide an improvement in the previous technique of determining isozyme accurately.

According to applicants' previous invention, differential estimation of m-GOT in samples were determined by using the purified s-GOT extracted from the serum or the tissue of mammals as an antigen. The substance to be examined was mixed with sensitized particles coupling an antiserum obtained by immunizing the mammal against the antigen with insoluble particles in an adequate buffer solution (i.e. about neutral to not destroy erythrocyte), and then removing immunoconjugate of s-GOT in the substance and anti-serum by separating said mixed solution by centrifuging.

According to this method, however, while the removal of s-GOT in human serum could be performed completely when immunized with purified human s-GOT as antigen, a small amount of unabsorbed s-GOT remained when using s-GOT as antigen which originated from other mammals. Accordingly, accurate measurement of m-GOT was not obtained, which is particularly unfortunate since the normal value of m-GOT in human serum is only zero to 5 Karmen units. Therefore, it has become especially important to find a method by which an accurate determination of m-GOT is possible even at low levels.

The present invention is, therefore, directed to a process for determining m-GOT accurately by absorbing the s-GOT in human serum completely with an anti-s-GOT antibody obtained by immunizing other mammals with purified s-GOT as an antigen extracted from the serum or the tissue of the mammal.

In other words, according to the present invention, m-GOT is differentially estimated by preparing an immunoconjugate by adding the anti-s-GOT antibody obtained by immunizing the mammal with s-GOT originating from mammals other than human into the sample (human serum) and then adding sensitized insoluble particles which are allowed to couple with the anti-s-GOT antibody.

By "sensitized particles" is meant carriers or coated particles such as red blood cells or latex particles coupled with either antigens or antibodies for the purpose of being used in immunological reaction.

The "insoluble particles" employed in the present invention are erythrocytes, cells of microorganism, polystyrene particles, copolymer dextran gel insoluble in water, cellulose powders, copolymer of divinyl benzene, aminopropyl glass, gelatine or the mixture thereof.

Any erythrocyte may be used if it is separated from the mammal and is stored in physiological saline. Suitable polystyrene particles are available under the name of "polystyrene latex" by Difco Company in U.S.A. The copolymer dextran gel, copolymer agarose and the like are also commercially available, called SEPHAROSE or SEPHADEX.

Representative coupling agents used in the present invention are bis-diazobenzidine, bis-diazobenzidine sulfonic acid, tetraazo-para-phenylene-diamine, difluoro-dinitro benzene, difluorodinitro-phenyl sulfonate carbodiimide, toluene isocyanate, cyanuric chloride, and dichloro-S-triazine.

In addition, cyano compounds such as cyanobromide, and tannic acid, the physical adsorbent, may be used as the coupling agents. Some of these coupling agents, especially cyanurization agent, dialdehyde and saturated or unsaturated $\alpha$-$\beta$-aldehyde, couple to the group on the surface of the cells, and at the same time, protect the cells of the erythrocyte and the microorganism. Therefore, these cells are stable to dissolution. When such coupling agents are used, there is no need to perform another stabilization or residual treatment. By using antibodies, insoluble particles and coupling agents of the present invention, the immunizing adsorbent which removes s-GOT is obtained. In addition, in accordance with the description of this invention s-GOT can be measured in reverse using m-GOT with insoluble particles.

The examples according to this invention are as follows:

EXAMPLE I

One ml of a suspension of anti-s-GOT serum sensitized blood cells was placed into a small test tube, washed with 5 ml physiological saline, the supernatant of which was discarded after centrifugation.

A solution of 0.6 ml containing known quantities of purified human s-GOT and m-GOT was added to a lyophilized anti-s-GOT antibody, and after standing for 5 minutes at room temperature, it was thoroughly shaken and stirred adding 0.5 ml of said solution to said anti-s-GOT serum sensitized blood cells and allowed to stand for 5 minutes additional at room temperature. Then, the level of m-GOT in the supernatant was measured with a method of UV absorption after separating with a centrifuge.

The results are shown in Table I

TABLE I

| Solution including s-GOT and m-GOT | s-GOT | 200 | 200 | 200 | 200 | 200 | 200 | 200 | 200 | 0 |
|---|---|---|---|---|---|---|---|---|---|---|
|  | m-GOT | 0 | 2 | 5 | 10 | 20 | 40 | 80 | 160 | 200 |
| m-GOT level of supernatant |  | 0 | 2 | 5 | 10 | 21 | 40 | 81 | 162 | 200 |

Remark: The unit is shown in Karmen units

EXAMPLE II

One ml suspension of anti-m-GOT serum sensitized blood cells was placed into a small test tube, washed with 5 ml physiological saline, the supernatant of which was discarded after centrifugation.

A solution of 0.6 ml containing known quantities of purified s-GOT and m-GOT was added to a lyophilized anti-m-GOT antibody, and after standing for 5 minutes at room temperature, it was thoroughly shaken and stirred adding 0.5 ml of said solution to said anti m-GOT serum sensitized blood cells and allowed to stand for 5 additional minutes at room temperature. Then, the level of s-GOT in the supernatant was measured with a method of UV absorption after separating with a centrifuge.

The results are shown in Table II.

TABLE II

| Solution including s-GOT and m-GOT | s-GOT | 200 | 200 | 200 | 200 | 200 | 200 | 200 | 200 | 0 |
|---|---|---|---|---|---|---|---|---|---|---|
|  | m-GOT | 0 | 2 | 5 | 10 | 20 | 40 | 80 | 160 | 200 |
| s-GOT level of supernatant |  | 200 | 200 | 202 | 200 | 198 | 201 | 200 | 202 | 0 |

Remark: The unit is shown in Karmen units

EXAMPLE III

The level of m-GOT and s-GOT in human serum was measured respectively with UV techniques using the anti-s-GOT lyophilized antibody and the anti-s-GOT serum sensitized blood cells, anti m-GOT lyophilized antibody and anti m-GOT serum sensitized blood cells respectively with the same methods as in EXAMPLES I and II. In addition, the total GOT level (m-GOT and s-GOT) was measured with UV method.

The results are shown in Table III.

TABLE III

| Sample | Total GOT level | s-GOT level | m-GOT level |
|---|---|---|---|
| blood serum 1 | 63 | 57 | 8 |
| blood serum 2 | 67 | 62 | 6 |
| blood serum 3 | 71 | 62 | 8 |
| blood serum 4 | 88 | 75 | 12 |
| blood serum 5 | 183 | 156 | 28 |
| blood serum 6 | 303 | 280 | 25 |

Remark: The unit is shown in Karmen units

What is claimed is:

1. A method for differential estimation of glutamic acid-oxalacetic acid transaminase (GOT) isozyme in human serum which comprises determining the m-GOT fraction by preparing an immuno conjugate thereof by adding anti-s-GOT antibody obtained by immunizing a non-human animal with a purified s-GOT antigen extracted from the blood or tissue of said mammal, adding anti-s-GOT serum and said immuno conjugate into said human serum; adding sensitized particles capable of coupling said anti-s-GOT antibody to insoluble particles, thereby absorbing completely said s-GOT in the human serum; separating said absorbed s-GOT from said m-GOT fraction, and determining the level of said m-GOT.

2. The method of claim 1, wherein the determination of m-GOT is carried out by UV absorbtion.

3. The method of claim 1, wherein said sensitized particles are red blood cells or latex particles coupled with antigens or antibodies.

4. The method of claim 1, wherein a coupling agent is employed to couple the antibodies and insoluble particles.